United States Patent
Chen

(10) Patent No.: US 9,616,125 B2
(45) Date of Patent: Apr. 11, 2017

(54) STABLE NOCATHIACIN LYOPHILIZED INJECTION AGENT

(71) Applicant: NANJING BIOTICA PHARMACEUTICAL COMPANY, Nanjing (CN)

(72) Inventor: Yijun Chen, Nanjing (CN)

(73) Assignee: NANJING BIOTICA PHARMACEUTICAL COMPANY (CN)

( * ) Notice: Subject to any disclaimer, the term of this patent is extended or adjusted under 35 U.S.C. 154(b) by 0 days.

(21) Appl. No.: 14/765,375

(22) PCT Filed: Sep. 12, 2013

(86) PCT No.: PCT/CN2013/083366
§ 371 (c)(1),
(2) Date: Aug. 3, 2015

(87) PCT Pub. No.: WO2014/121611
PCT Pub. Date: Aug. 14, 2014

(65) Prior Publication Data
US 2015/0374824 A1    Dec. 31, 2015

(30) Foreign Application Priority Data
Feb. 5, 2013    (CN) .......................... 2013 1 0044818

(51) Int. Cl.
| | | |
|---|---|---|
| A61K 38/14 | (2006.01) | |
| A61K 47/10 | (2017.01) | |
| A61K 38/12 | (2006.01) | |
| A61K 47/26 | (2006.01) | |
| A61K 9/19 | (2006.01) | |
| A61K 9/00 | (2006.01) | |
| A61K 47/34 | (2017.01) | |

(52) U.S. Cl.
CPC ............ *A61K 47/10* (2013.01); *A61K 9/0019* (2013.01); *A61K 9/19* (2013.01); *A61K 38/12* (2013.01); *A61K 38/14* (2013.01); *A61K 47/26* (2013.01); *A61K 47/34* (2013.01)

(58) Field of Classification Search
CPC ........ A61K 38/00; A61K 38/02; A61K 38/03; A61K 38/04; A61K 38/05; A61K 38/12; A61K 38/14; A61K 47/10; A61K 47/26; C07K 9/003
See application file for complete search history.

(56) References Cited

U.S. PATENT DOCUMENTS

| | | | | |
|---|---|---|---|---|
| 8,436,190 | B2* | 5/2013 | Brittain | A61K 9/0019 34/284 |
| 2004/0042972 | A1* | 3/2004 | Truong-Le | A61K 9/0043 424/46 |
| 2007/0116729 | A1* | 5/2007 | Palepu | A61K 9/19 424/400 |
| 2008/0132500 | A1* | 6/2008 | Liu | C07D 515/22 514/233.2 |
| 2012/0014978 | A1* | 1/2012 | Hafner | A61K 9/19 424/185.1 |

FOREIGN PATENT DOCUMENTS

CN    102018953 B  *  5/2013

OTHER PUBLICATIONS

Baheti et al. Excipients used in lyophilization of small molecules. Journal of Excipients and Food Chemistry. 2010, vol. 1, No. 1, pp. 41-54.*

* cited by examiner

*Primary Examiner* — Jeffrey E Russel
(74) *Attorney, Agent, or Firm* — Schmeiser, Olsen & Watts, LLP

(57) ABSTRACT

A stable and lyophilized pharmaceutical agent containing nocathiacin, which is prepared by lyophilizing a liquid formulation of nocathiacin, a stabilizer, an excipient, a pH regulator and injectable water, wherein the stabilizer is selected from polyethylene glycol, polysorbate or a mixture thereof, and the pH value of the liquid formulation is 1.0-6.0 is provided.

10 Claims, 1 Drawing Sheet

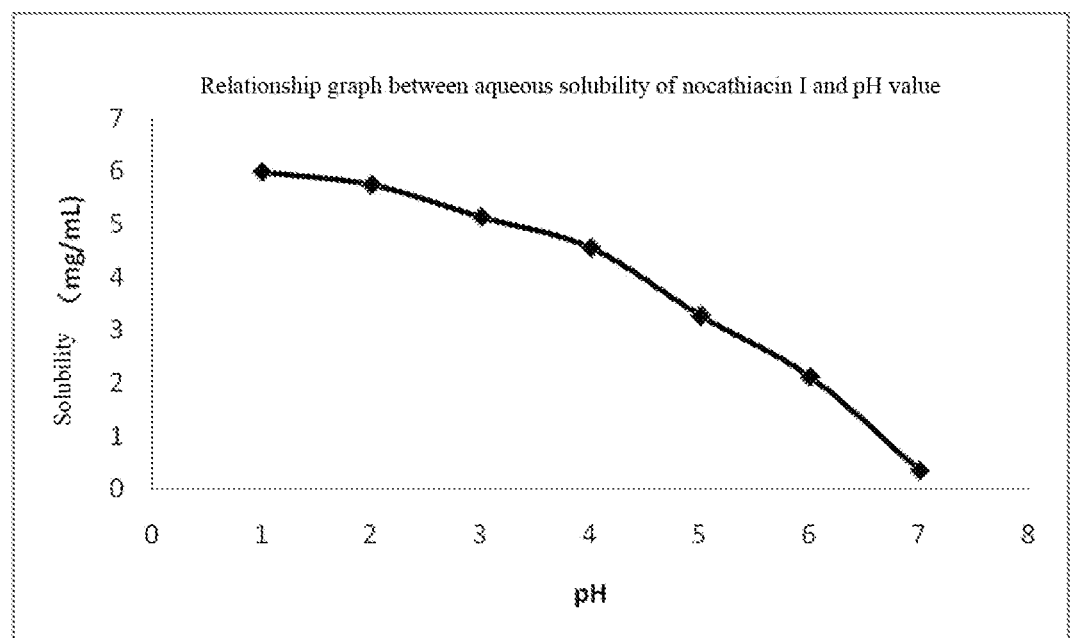

STABLE NOCATHIACIN LYOPHILIZED INJECTION AGENT

CROSS-REFERENCE TO RELATED APPLICATIONS

This application claims priority to PCT Application No. PCT/CN2013/083366, having a filing date of Sep. 12, 2013, based off of Chinese Application No. 201310044818.9, having a filing date of Feb. 5, 2013 the entire contents of which are hereby incorporated by reference.

FIELD OF TECHNOLOGY

The following belongs to the field of therapeutic medicines, and particularly relates to a stable and lyophilized pharmaceutical agent containing nocathiacin.

BACKGROUND

Nocathiacin is a type of novel agent against multi-drug resistant bacteria, which is isolated from a soil microorganism and has novel structure and significant antibacterial activity. It is one of those thiopeptide antibiotics showing most potential in clinic application (see: J. Antibiot. 2003, 26:232-242). As a common characteristic of the thiopeptide antibiotics, the nocathiacin has a special high-hydrophobic ring system similar to other antibiotics in the same group, which possesses an extremely poor water solubility. In order to improve the water solubility of nocathiacin, a great number of series chemical and biological modification and transformation studies direct to the hydroxyl groups on the dehydroalanine side chain, indole and pyridyl rings of nocathiacin have been conducted, which are all failed due to such factors as complicated preparation and safety issues (see: J Org Chem, 2002, 67(24):8699-8702; J Nat Prod, 2005, 68(4):550-553; Bioorg Med Chem Lett, 2004, 14(14): 3743-3746).

However, it is reported in literatures that nocathiacin possesses super-strong antibacterial activities against most gram-positive bacteria, particularly methicillin-resistant *staphylococcus aureus* (MRSA), penicillin-resistant *streptococcus pneumoniae* (PRSP), vancomycin-resistant *enterococcus* (VRE) and *mycobacterium tuberculosis* with effective concentration in a level less than 1 μg/ml; (see: J. Antibiot. 2003, 56:226-231). This shows that nocathiacin in clinic can be implemented by using low dose of nocathiacin. For the medicines with low doses in clinical application, the problem of low solubility could be relatively feasible to be solved through a pharmaceutical preparation because of the ease of increasing the solubility to a small degree with various approaches, and this problem may not become a key factor to limit its clinic application. On the other hand, as a cyclopeptide compound, the stability of nocathiacin is a major obstacle to be overcome for pharmaceutical usefulness. Therefore, the combination of solving the issues on both solubility and stability is challenging, which requires extensive investigation.

The Chinese patent (application No.: 201010548129.8) under the title of "Nocathiacin Antibiotic Drug Composition Containing Emulsifying Agent" discloses a drug composition containing nocathiacin and a drug carrier, and further includes a water-soluble emulsifying agent and a lipophilic emulsifying agent, wherein the drug carrier is composed of an aqueous phase and an organic phase. The Chinese patent (application No.: 201010548142.3) under the title of "Drug Composition of Nocathiacin Antibiotics Containing Lipid Material" discloses a drug composition containing nocathiacin antibiotics, which mainly includes the principal drug nocathiacin and the lipid material, wherein the lipid material is selected from phospholipid or cholesterol. And the Chinese patent (application No.: 201010548134.9) under the title of "Drug Composition Containing Nocathiacin Antibiotics" specifically discloses a drug composition containing nocathiacin antibiotics, which includes nocathiacin, a drug carrier and a hydrotropic substance, wherein the hydrotropic substance is selected from latent solvent or solubilizer; and the drug carrier is a physiologically dissolving medium with a pH of 4-9. Different preparations are respectively used in the above-mentioned patents to improve the solubility of nocathiacin. However, all the above-mentioned patents relate to liquid preparations of nocathiacin, which only address the poor solubility of nocathiacin, but do not deal with the stability of nocathiacin. As a thiopeptide compound, nocathiacin is sensitive to various environmental factors such as moistness, heat, light and the like, and is easy to degrade; therefore, it is very necessary to obtain a stable pharmaceutical agent containing nocathiacin while improving the solubility of nocathiacin at present.

There are multiple factors that affect the activity of protein or peptide drugs, which mainly include two aspects, wherein one aspect refers to structural factors including molecular weight, amino acid composition, amino acid sequence, presence of disulfide linkage, position of disulfide linkage, and 3-dimensional structure; the second aspect refers to peripheral environmental factors of the macromolecules, where changes like coagulation, precipitation, hydrolysis and deamidating will occur to the proteins or peptides due to the influences of complicated physical and chemical factors. Lyophilization refers to a drying method of freezing the drugs under a low temperature, lyophilizing the drugs under a vacuum condition to remove crystal ice, and performing desorption drying to remove partial bound water after the ending of sublimation. The lyophilizing technology can keep the activity of proteins and peptides for a long term because of the moderate condition and lower moisture content in the finished products. Therefore, lyophilized preparations are mostly applied to protein or peptide drugs.

Compared with other preparation methods, the lyophilization has the following advantages:
1) the liquid pharmaceutical formulation is sub-packed conveniently and accurately before lyophilizing, so that continued production can be achieved; 2) the processing condition is moderate, and drying is performed under low temperature with low pressure, which is beneficial for keeping the activity of temperature-sensitive substances, and can avoid the decomposition and degeneration under high temperature and high pressure, so that the drugs will not be denatured; 3) the moisture content is low, where the moisture content of the lyophilized product is generally 1%-3%; meanwhile, the product can be even dried and stored in case of nitrogen gas protection in vacuum, and cannot be easily oxidized, thus being beneficial for long distance transportation and long term storage; 4) the product has an excellent appearance, which is a porous loose structure and the color does not change substantially, and the rehydration characteristics are good, enabling the lyophilized drugs to absorb water quickly so as to be reduced to a state before being lyophilized; and 5) a lyophilizing device is operated closely, and the installation environment has high cleanness, which reduces the possibility of contamination by microorganisms, particulate, dry and neutralize anoxia after packing, and can play the roles of sterilizing and suppressing bacterial viability.

However, when the lyophilized preparation is applied to the peptide and protein drugs, requirements on selecting accessories are very strict; and inappropriate selection of the accessories will cause instability of the product to result in the loss of activity. Moreover, a solvent for preparing the liquid pharmaceutical formulation before lyophilizing cannot be selected randomly, and is only limited to water or organic solvents having higher freezing point. Sometimes, a turbidness phenomenon will occur to the lyophilized product while re-dissolving it, and this has to be considered and researched by experiments for developing the lyophilized preparation.

At present, no studies on lyophilized pharmaceutical agent containing nocathiacin and its stability have been reported in literatures.

SUMMARY

An aspect relates to a stable and lyophilized pharmaceutical agent containing nocathiacin while improving the solubility of nocathiacin.

A stable and lyophilized pharmaceutical agent containing nocathiacin is prepared by lyophilizing a liquid formulation of nocathiacin, a stabilizer, an excipient, a pH regulator and injectable water, wherein the stabilizer is selected from polyethylene glycol, polysorbate or a mixture thereof, and pH value of the liquid formulation is 1.0-6.0.

The percentage of weight against volume of the foregoing nocathiacin to the liquid formulation is 0.005%-2%.

The percentage of weight against volume of the foregoing stabilizer to the liquid formulation is 6%-30%, and is preferably 8%-18%.

The type and amount used of the foregoing excipient are the type and regularly used amount that are well-known to those skilled in the art, wherein the excipient is preferably selected from one or more of sodium chloride, glucose, lactose, mannitol, trehalose, xylitol, cane sugar, sorbitol, dextran, albumin, hydroxyethyl starch and glycine, and the percentage of weight against volume of the excipient to the liquid formulation is preferably 5%-50%, and the more preferable percentage of weight against volume of the excipient to the liquid formulation is 5%-30%.

The foregoing pH regulator is of the type well-known to those skilled in the art, which is selected from one or more of hydrochloric acid, citric acid, phosphoric acid, lactic acid, tartaric acid and succinic acid, and the amount of solution used is to adjust pH value to pH 1-6.

The stable and lyophilized pharmaceutical agent containing nocathiacin according to embodiments of the present invention further include a buffer, wherein the buffer is selected from one or more of citrate, lactate, acetate, tartrate, succinate and phosphate, and the amount of the buffer used is regularly used by those skilled in the art, which is preferably 0.04%-1.0%.

The nocathiacin according to embodiments of the present invention is selected from nocathiacin I, nocathiacin II or nocathiacin III.

The specification of nocathiacin in the lyophilized pharmaceutical agent according to embodiments of the present invention is 0.1 mg-100 mg.

The polyethylene glycol according to embodiments of the present invention is selected from one or more of polyethylene glycol 200, polyethylene glycol 300, polyethylene glycol 400 and polyethylene glycol 600.

The polysorbate according to embodiments of the present invention is selected from one or more of polysorbate 20, polysorbate 40, polysorbate 60 and polysorbate 80.

According to the above lyophilized pharmaceutical agent containing nocathiacin, the preferable pH of the liquid formulation is 2.0-5.0, and the more preferable pH of the liquid formulation is 2.0-3.5.

Under a physiological pH condition, the solubility of nocathiacin is only approximately 0.1 µg/ml. In embodiments of the present invention, the pH-dependent characteristic of the solubility of nocathiacin is utilized to properly reduce pH value through a pH regulator and improve the solubility of nocathiacin in aqueous solution.

It is found during the formulation process of embodiments of the present invention that 6-30% polyethylene glycol or polysorbate or a combination thereof can improve the re-dissolving performance of the lyophilized agent and the stability of nocathiacin.

The Chinese patent (application No.: 201010548134.9) under the title of "Drug Composition Containing Nocathiacin Antibiotics" includes a solution of using polyethylene glycol (PEG) as a latent solvent and using polysorbate as a solubilizer, but polyethylene glycol in the patent can have a preferable hydration effect only under a higher concentration. However, because the melting temperature of PEG is low, the excessive content of PEG will cause the product to be difficultly lyophilized and have poor forming performance. In addition, when the volume fraction of PEG in an injection product is greater than 40%, a hemolysis phenomenon can be observed. The amount of polysorbate used in the patent is very low, which only plays the role of solubilizing the drug, but cannot play the roles of stabilizing the agent form and keeping the activity of the drug.

The lyophilized pharmaceutical agent containing nocathiacin according to embodiments of the present invention can be prepared using a regular lyophilizing method, and is preferably prepared through a method as follows:

(1) preparing a nocathiacin liquid formulation:

(1a) dissolving 0.005%-2% nocathiacin in 6%-30% polyethylene glycol or polysorbate or a combination thereof or a correspondingly saturated aqueous solution according to the volume of the final liquid formulation in the formulated amount and according to the percentage of weight against volume;

(1b) dissolving the pH regulator and the excipient or the pH regulator and the excipient and other accessories into injectable water which is 80% to the final volume of the liquid formulation; and (1c) supplementing water to the formulated amount for injection, mixing evenly, sterilizing and filtering, and then encapsulating;

(2) lyophilizing the nocathiacin liquid formulation:

(2a) pre-freezing: reducing the temperature of the nocathiacin liquid formulation to −40±2° C., and then keeping the temperature for 2-4 h to obtain a pre-frozen product;

(2b) lyophilizing: starting a vacuum pump, controlling the degree of vacuum in a lyophilizing tank to be less than 20 Pa, increasing the temperature of a shelf to −20±2° C., and keeping the temperature for 6-8 h; then increasing the temperature of the shelf to 0±2° C., and keeping the temperature for 2-4 h; and (2c) secondary drying: keeping the temperature of the shelf at 0±2° C., reducing the degree of vacuum in the lyophilizing tank to be less than 5 Pa and maintaining for 24 h, then increasing the temperature of the lyophilized product to 25±2° C., and reducing the degree of vacuum in the lyophilizing tank to be less than 3 Pa at the same time, and maintaining the temperature for 8-12 h to prepare the lyophilized pharmaceutical agent containing nocathiacin.

Compared to prior art, embodiments of the present invention have the following advantages:

1. The stable and lyophilized pharmaceutical agent containing nocathiacin can be obtained while improving the solubility of nocathiacin at the same time without the requirement of performing complicated preparations such as emulsion, liposome, superamolecule and microspheres through using the pH regulator and the stabilizer.

2. The content of polyethylene glycol used in embodiments of the present invention is lower than that reported in literature, which not only enables the product to have better forming performance, but also reduces the hemolysis risk caused by polyethylene glycol. Moreover, the stabilizer used in embodiments of the present invention also has the effect of solubilizing at the same time, which reduces the number and quantity of accessories, and is more beneficial for product safety.

3. The formulation and process of the product according to embodiments of the present invention are simple and easy, and are beneficial for commercial and large-scale production. No organic solvents are used in the process, which is beneficial for the environment and safety.

4. Given that the present studies on nocathiacin mainly focus on the aspect of improving the solubility of nocathiacin, embodiments of the present invention solves the issues of chemical stability of nocathiacin in preparations while improving the solubility of nocathiacin at the same time, which makes it possible to successfully apply nocathiacin in patients for therapeutic purposes. Through screening the prescriptions, and in particular, embodiments of the present invention provide a stable drug composition, which is prepared by a mixture of 0.005%-2% nocathiacin, 6%-30% stabilizer and a pH regulator with a lyophilizing method. The nocathiacin content of the composition after being sealed and placed for six months under 25° C. and a relative humidity of 60% is greater than 90% of that before placing.

BRIEF DESCRIPTION

FIG. 1 is a relationship graph between aqueous solubility of nocathiacin I and pH value.

DETAILED DESCRIPTION

The following will be further described hereinafter with reference to the specific embodiments. It should be appreciated that the embodiments are for explanation only, but not intended to restrict the scope of embodiments of the present invention. It should be further appreciated that those skilled in the art may make various alternations or modifications on embodiments of the present invention after reading the contents taught by embodiments of the present invention, and these equivalent forms shall also similarly fall within the scope defined by the appended claims of embodiments of the present invention.

Embodiment 1

Relationship Between Aqueous Solubility of Nocathiacin I and pH Value

Excessive purified material of nocathiacin I is added in test tubes with stopper respectively, and a certain amounts of buffer solutions with pH 2, pH 3, pH 4, pH 5, pH 6 and pH 7 are added to ensure that the solutions are in a supersaturated state all the time, and the solutions are shaken for 24 h under room temperature. Then the solutions are filtered through a 0.22 millipore filter, and the subsequent filtrate is taken and fed in a high performance liquid chromatography to measure the drug contents. The chromatogram conditions are as follows.

Chromatographic column: Waters Symmetry, 150 mm×4.6 mm, 5 μm.

Mobile phase: A. distilled water containing 0.05% TFA; and B. acetonitrile containing 0.05% TFA.

Gradient: Gradient elution for 32 min, 30%-60% B.

Column temperature: 40° C., and rate of flow: 1 ml/min

Detection wavelength: 362 nm, and sample volume: 10 μl.

As shown in FIG. 1, the solubility of nocathiacin I decreases with the increase of pH value within a scope of pH 1-7. A nocathiacin I solution having a concentration more than 0.5 mg/mL can be obtained when pH value of the liquid formulation is controlled below 6.

Embodiment 2

Screening of Stabilizer

Prescription constituents employed are as follows:

| Prescription constituent | Amount used (g) |
|---|---|
| Nocathiacin I | 10 |
| Acetic acid | 5.2 |
| Sodium acetate | 9 |
| Stabilizer | 150 |
| Mannitol | 200 |

Process: weigh nocathiacin I and stabilizer according to the formulated amount, and stir for dissolution; weigh other accessories according to the formulated amount. After adding 800 mL injectable water, stir for resolution. Then, mix the two solutions, and adjust pH to 3.0, supplement injectable water to 1000 mL, use a 0.22 μm millipore filter to filter, sub-pack, and lyophilize, thus obtaining lyophilized pharmaceutical agent containing nocathiacin.

The re-dissolving stabilities of lyophilized products prepared by different stabilizers are summarized, wherein the results are as shown in Table 1.

Table 1 Influences of stabilizer type on the re-dissolving stability of nocathiacin I lyophilized product

TABLE 1

Influences of stabilizer type on the re-dissolving stability of nocathiacin I lyophilized product

| Stabilizer type | State after re-dissolving | State of standing for 1 h after re-dissolving | State of standing for 3 h after re-dissolving |
|---|---|---|---|
| Polyvidone K30 | Clear | Clear | Precipitation found |
| Polyvidone K90 | Clear | Precipitation found | Precipitation found |
| Gum arabic | Clear | Clear | Precipitation found |

TABLE 1-continued

Influences of stabilizer type on the re-dissolving stability of nocathiacin I lyophilized product

| Stabilizer type | State after re-dissolving | State of standing for 1 h after re-dissolving | State of standing for 3 h after re-dissolving |
|---|---|---|---|
| Sodium dodecyl | Clear | Precipitation found | Precipitation found |
| Polysorbate 80 | Clear | Clear | Clear |
| Polysorbate 60 | Clear | Clear | Clear |
| Polysorbate 40 | Clear | Clear | Clear |
| Polysorbate 20 | Clear | Clear | Clear |
| Gelatin | Clear | Clear | Precipitation found |
| Polyethylene glycol | Clear | Clear | Clear |
| Hydroxypropyl methyl cellulose E5 | Clear | Precipitation found | Precipitation found |
| Polyethylene glycol 600 | Clear | Clear | Clear |
| Polyethylene glycol | Clear | Clear | Clear |
| Polyethylene glycol | Clear | Clear | Clear |

The results show that the re-dissolving stability is best when polyethylene glycol and polysorbate accessories are served as a stabilizer.

Embodiment 3

| Prescription constituent | Amount used (g) |
|---|---|
| Nocathiacin I | 0.05 |
| Phosphoric acid | 10.2 |
| Disodium hydrogen phosphate | 10 |
| Polysorbate 20 | 60 |
| Sorbitol | 100 |

Process: weigh nocathiacin I and stabilizer according to the formulated amount, and stir for resolution; weigh other accessories according to the formulated amount, add 800 mL injectable water, and stir for resolution; mix the two solutions, and adjust pH to 2.0, supplement injectable water to 1000 mL, use a 0.22 μm millipore filter to filter, sub-pack, and lyophilize, thus obtaining lyophilized pharmaceutical agent containing nocathiacin.

Embodiment 4

| Prescription constituent | Amount used (g) |
|---|---|
| Nocathiacin I | 20 |
| Citric acid | 3.9 |
| Sodium citrate | 0.4 |
| Polysorbate 80 | 80 |
| Mannitol | 150 |

Process: weigh nocathiacin I and stabilizer according to the formulated amount, and stir for resolution; weigh other accessories according to the formulated amount, add 800 mL injectable water, and stir for resolution; mix the two solutions, and adjust pH to 3.0, supplement injectable water to 1000 mL, use a 0.22 μm millipore filter to filter, sub-pack, and lyophilize, thus obtaining lyophilized pharmaceutical agent containing nocathiacin.

Embodiment 5

| Prescription constituent | Amount used (g) |
|---|---|
| Nocathiacin I | 1.0 |
| Acetic acid | 5.2 |
| Sodium acetate | 5 |
| Polyethylene glycol 20 | 180 |
| Mannitol | 200 |

Process: weigh nocathiacin I and stabilizer according to the formulated amount, and stir for resolution; weigh other accessories according to the formulated amount, add 800 mL injectable water, and stir for resolution; mix the two solutions, and adjust pH to 3.0, supplement injectable water to 1000 mL, use a 0.22 μm millipore filter to filter, sub-pack, and lyophilize, thus obtaining lyophilized pharmaceutical agent containing nocathiacin.

Embodiment 6

| Prescription constituent | Amount used (g) |
|---|---|
| Nocathiacin I | 10 |
| Hydrochloric acid | 3 |
| Polyethylene glycol 400 | 300 |
| Lactose | 300 |
| Glycine | 200 |

Process: weigh nocathiacin I and stabilizer according to the formulated amount, and stir for resolution; weigh other accessories according to the formulated amount, add 800 mL injectable water, and stir for resolution; mix the two solutions, and adjust pH to 5.0, supplement injectable water to 1000 mL, use a 0.22 μm millipore filter to filter, sub-pack, and lyophilize, thus obtaining lyophilized pharmaceutical agent containing nocathiacin.

Embodiment 7

| Prescription constituent | Amount used (g) |
|---|---|
| Nocathiacin I | 7.5 |
| Citric acid | 4.6 |

-continued

| Prescription constituent | Amount used (g) |
|---|---|
| Sodium citrate | 0.5 |
| Polyethylene glycol 200 | 150 |
| Polysorbate 60 | 100 |
| Glucose | 250 |

Process: weigh nocathiacin I and stabilizer according to the formulated amount, and stir for resolution; weigh other accessories according to the formulated amount, add 800 mL injectable water, and stir for resolution; mix the two solutions, and adjust pH to 3.5, supplement injectable water to 1000 mL, use a 0.22 μm millipore filter to filter, sub-pack, and lyophilize, thus obtaining lyophilized pharmaceutical agent containing nocathiacin.

Embodiment 8

| Prescription constituent | Amount used (g) |
|---|---|
| Nocathiacin I | 15 |
| Lactic acid | 5 |
| Sodium lactate | 0.5 |
| Polyethylene glycol 600 | 150 |
| Polysorbate 40 | 50 |
| Glucose | 50 |

Process: weigh nocathiacin I and stabilizer according to the formulated amount, and stir for resolution; weigh other accessories according to the formulated amount, add 800 mL injectable water, and stir for resolution; mix the two solutions, and adjust pH to 4.0, supplement injectable water to 1000 mL, use a 0.22 μm millipore filter to filter, sub-pack, and lyophilize, thus obtaining lyophilized pharmaceutical agent containing nocathiacin.

Embodiment 9

| Prescription constituent | Amount used (g) |
|---|---|
| Nocathiacin I | 2.5 |
| Lactic acid | 5 |
| Sodium lactate | 0.5 |
| Polyethylene glycol 400 | 50 |
| Polysorbate 80 | 25 |
| Dextran | 100 |

Process: weigh nocathiacin I and stabilizer according to the formulated amount, and stir for resolution; weigh other accessories according to the formulated amount, add 800 mL injectable water, and stir for resolution; mix the two solutions, and adjust pH to 4.0, supplement injectable water to 1000 mL, use a 0.22 μm millipore filter to filter, sub-pack, and lyophilize, thus obtaining lyophilized pharmaceutical agent containing nocathiacin.

Embodiment 10

| Prescription constituent | Amount used (g) |
|---|---|
| Nocathiacin I | 10 |
| Hydrochloric acid | 3 |
| Polysorbate 80 | 80 |
| Polyethylene glycol 400 | 100 |

-continued

| Prescription constituent | Amount used (g) |
|---|---|
| Lactose | 150 |
| Glycine | 150 |

Process: weigh nocathiacin I and stabilizer according to the formulated amount, and stir for resolution; weigh other accessories according to the formulated amount, add 800 mL injectable water, and stir for resolution; mix the two solutions, and adjust pH to 1.0, supplement injectable water to 1000 mL, use a 0.22 μm millipore filter to filter, sub-pack, and lyophilize, thus obtaining lyophilized pharmaceutical agent containing nocathiacin.

Embodiment 11

| Prescription constituent | Amount used (g) |
|---|---|
| Nocathiacin I | 0.5 |
| Hydrochloric acid | 3 |
| Polyethylene glycol 400 | 60 |
| Dextran | 70 |

Process: weigh nocathiacin I and stabilizer according to the formulated amount, and stir for resolution; weigh other accessories according to the formulated amount, add 800 mL injectable water, and stir for resolution; mix the two solutions, and adjust pH to 3.0, supplement injectable water to 1000 mL, use a 0.22 μm millipore filter to filter, sub-pack, and lyophilize, thus obtaining lyophilized pharmaceutical agent containing nocathiacin.

Embodiment 12

| Prescription constituent | Amount used (g) |
|---|---|
| Nocathiacin I | 5.0 |
| Citric acid | 4.6 |
| Sodium citrate | 0.5 |
| Polyethylene glycol 200 | 100 |
| Polysorbate 60 | 150 |
| Glucose | 250 |

Process: weigh nocathiacin I and stabilizer according to the formulated amount, and stir for resolution; weigh other accessories according to the formulated amount, add 800 mL injectable water, and stir for resolution; mix the two solutions, and adjust pH to 6.0, supplement injectable water to 1000 mL, use a 0.22 μm millipore filter to filter, sub-pack, and lyophilize, thus obtaining lyophilized pharmaceutical agent containing nocathiacin.

Comparison Example 1

Excluding Stabilizer

| Prescription constituent | Amount used (g) |
|---|---|
| Nocathiacin I | 5 |
| Hydrochloric acid | 3 |
| Dextran | 90 |

Process: weigh nocathiacin I and stabilizer according to the formulated amount, and stir for resolution; weigh other accessories according to the formulated amount, add 800 mL injectable water, and stir for resolution; mix the two solutions, and adjust pH to 2.0, supplement injectable water to 1000 mL, use a 0.22 μm millipore filter to filter, sub-pack, and lyophilize, thus obtaining lyophilized pharmaceutical agent containing nocathiacin.

Comparison Example 2

Excluding Stabilizer

| Prescription constituent | Amount used (g) |
|---|---|
| Nocathiacin I | 5 |
| Acetic acid | 5.2 |
| Sodium acetate | 6 |
| Mannitol | 100 |

Process: weigh nocathiacin I and stabilizer according to the formulated amount, and stir for resolution; weigh other accessories according to the formulated amount, add 800 mL injectable water, and stir for resolution; mix the two solutions, and adjust pH to 3.0, supplement injectable water to 1000 mL, use a 0.22 μm millipore filter to filter, sub-pack, and lyophilize, thus obtaining lyophilized pharmaceutical agent containing nocathiacin.

Comparison Example 3

The Content of Stabilizer is Higher than 30%

| Prescription constituent | Amount used (g) |
|---|---|
| Nocathiacin I | 10 |
| Acetic acid | 5.2 |
| Sodium acetate | 6 |
| Polyethylene glycol 400 | 350 |
| Mannitol | 300 |

Process: weigh nocathiacin I and stabilizer according to the formulated amount, and stir for resolution; weigh other accessories according to the formulated amount, add 800 mL injectable water, and stir for resolution; mix the two solutions, and adjust pH to 3.0, supplement injectable water to 1000 mL, use a 0.22 μm millipore filter to filter, sub-pack, and lyophilize, thus obtaining lyophilized pharmaceutical agent containing nocathiacin.

Embodiment 13

Re-dissolving characteristics of nocathiacin I lyophilized agent The lyophilized agents are prepared by each comparison example and embodiment, and are re-dissolved, stood for 3 h, and then the appearance after the re-dissolving is observed, wherein the results are as shown in Table 2.

Table 2 Re-dissolving characteristics of the samples of the comparison examples an d embodiments

TABLE 2

Re-dissolving characteristics of the samples of the comparison examples and embodiments

| Example | Appearance of lyophilized product | State after re-dissolving | State of standing for 1 h after re-dissolving | State of standing for 3 h after re-dissolving |
|---|---|---|---|---|
| Comparison example 1 | White loose lumpy solid | Turbid | Precipitation found | Precipitation found |
| Comparison example 2 | White loose lumpy solid | Turbid | Precipitation found | Precipitation found |
| Comparison example 3 | White pasty semisolid | Clear | Clear | Clear |
| Embodiment 3 | White loose lumpy solid | Clear | Clear | Clear |
| Embodiment 4 | White loose lumpy solid | Clear | Clear | Clear |
| Embodiment 5 | White loose lumpy solid | Clear | Clear | Clear |
| Embodiment 6 | White loose lumpy solid | Clear | Clear | Clear |
| Embodiment 7 | White loose lumpy solid | Clear | Clear | Clear |
| Embodiment 8 | White loose lumpy solid | Clear | Clear | Clear |
| Embodiment 9 | White loose lumpy solid | Clear | Clear | Clear |
| Embodiment 10 | White loose lumpy solid | Clear | Clear | Clear |
| Embodiment 11 | White loose lumpy solid | Clear | Clear | Clear |

The results in Table 2 show that the re-dissolving characteristics of the lyophilized pharmaceutical agent containing nocathiacin excluding a stabilizer in the liquid formulation before lyophilizing is poor (comparison examples 1 and 2); while although the re-dissolving performance of the lyophilized agent containing nocathiacin greater than 30% stabilizer (comparison 3) is good, the lyophilized product is in a pasty semisolid shape, thus causing a poor forming performance.

Embodiment 14

Taking the embodiments 3, 9, and 11 for example, the lyophilized pharmaceutical agent containing nocathiacin excluding a stabilizer (comparison examples 1 and 2) and including a stabilizer (embodiments 3, 9 and 11) are placed under a temperature of 25° C. and a relative humidity RH lower than 60% for sixth months, and samples are taken respectively in the first month, the second month, the third month and the sixth month to measure the contents of related degradation substances with high performance liquid chromatography according to the method described in embodiment 1, wherein the results are as shown in Table 3.

TABLE 3

Influences of stabilizer on the stability of nocathiacin in the lyophilized agent

| Sampling time | Related degradation substance (%) | | | | |
|---|---|---|---|---|---|
| | Comparison example 1 | Comparison example 2 | Embodiment 3 | Embodiment 9 | Embodiment 11 |
| 0 month | 0.29 | 0.34 | 0.31 | 0.35 | 0.27 |
| 1 month | 2.22 | 2.08 | 0.64 | 0.70 | 0.59 |
| 2 months | 3.77 | 3.59 | 0.95 | 0.98 | 0.88 |
| 3 months | 4.92 | 4.96 | 1.20 | 1.19 | 1.12 |
| 6 months | 7.79 | 8.08 | 1.81 | 1.92 | 1.78 |

The results show that the use of the stabilizer can apparently improve the stability of the nocathiacin I in the lyophilized agent.

The invention claimed is:

1. A lyophilized pharmaceutical agent containing nocathiacin, prepared by lyophilizing a liquid formulation of nocathiacin, a stabilizer, an excipient, a pH regulator and injectable water, wherein the stabilizer is selected from polyethylene glycol, polysorbate or a mixture thereof, and the pH value of the liquid formulation ranges from 1.0 to 6.0.

2. The lyophilized pharmaceutical agent containing nocathiacin according to claim 1, wherein the percentage of weight against volume of the nocathiacin to the liquid formulation is 0.005%-2%.

3. The lyophilized pharmaceutical agent containing nocathiacin according to claim 1, wherein the percentage of weight against volume of the stabilizer to the liquid formulation is 6%-30%.

4. The lyophilized pharmaceutical agent containing nocathiacin according to claim 3, wherein the percentage of weight against volume of the stabilizer to the liquid formulation is 8%-18%.

5. The lyophilized pharmaceutical agent containing nocathiacin according to claim 1, wherein the percentage of weight against volume of the excipient to the liquid formulation is 5%-50%.

6. The lyophilized pharmaceutical agent containing nocathiacin according to claim 1, further comprising a buffer, wherein the buffer is selected from one or more of citrate, lactate, acetate, tartrate, succinate and phosphate.

7. The lyophilized pharmaceutical agent containing nocathiacin according to any one of claims 1 to 6, wherein the polyethylene glycol is selected from one or more of polyethylene glycol 200, polyethylene glycol 300, polyethylene glycol 400 and polyethylene glycol 600, and the polysorbate is selected from one or more of polysorbate 20, polysorbate 40, polysorbate 60 and polysorbate 80.

8. The lyophilized pharmaceutical agent containing nocathiacin according to any one of claims 1 to 6, wherein the pH value of the liquid formulation is 2.0-5.0.

9. The lyophilized pharmaceutical agent containing nocathiacin according to any one of claims 1 to 6, wherein the pH regulator is selected from one or more of hydrochloric acid, citric acid, phosphoric acid, lactic acid, tartaric acid and succinic acid.

10. The lyophilized pharmaceutical agent containing nocathiacin according to any one of claims 1 to 6, wherein the excipient is selected from one or more of sodium chloride, glucose, lactose, mannitol, trehalose, xylitol, cane sugar, sorbitol, dextran, albumin, hydroxyethyl starch and glycine.

* * * * *